(12) United States Patent
Allen et al.

(10) Patent No.: US 6,773,455 B2
(45) Date of Patent: Aug. 10, 2004

(54) STENT WITH REINFORCED STRUTS AND BIMODAL DEPLOYMENT

(75) Inventors: Richard T. Allen, Palo Alto, CA (US); Daniel L. Cox, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/848,819

(22) Filed: May 3, 2001

(65) Prior Publication Data

US 2001/0016770 A1 Aug. 23, 2001

Related U.S. Application Data

(63) Continuation of application No. 08/881,059, filed on Jun. 24, 1997, now abandoned.

(51) Int. Cl.⁷ .................................................. A61F 2/06
(52) U.S. Cl. ...................................................... 623/1.15
(58) Field of Search ................................ 623/1.1, 1.11, 623/1.12, 1.13, 1.15, 1.16

(56) References Cited

U.S. PATENT DOCUMENTS

| | | |
|---|---|---|
| 3,105,492 A | 10/1963 | Jeckel |
| 3,657,744 A | 4/1972 | Ersek |
| 3,868,956 A | 3/1975 | Alfidi et al. |
| 3,993,078 A | 11/1976 | Bergentz et al. |

(List continued on next page.)

FOREIGN PATENT DOCUMENTS

| | | |
|---|---|---|
| DE | A 36 40 745 | 6/1987 |
| EP | 0 540 290 A2 | 10/1992 |
| EP | 0 679 373 A | 11/1995 |
| EP | 0 712 614 A1 | 11/1995 |
| EP | 0 758 541 A1 | 8/1996 |
| EP | 0 758 541 A | 2/1997 |
| EP | 0 864 302 A2 | 3/1998 |
| GB | 2 135 585 A | 9/1984 |
| JP | 57-89859 | 6/1982 |
| JP | 8-336597 | 10/1991 |
| JP | 6-181993 | 11/1994 |
| JP | 9-26015 | 1/1997 |
| JP | 9-56824 | 3/1997 |
| WO | WO/89 01798 | 3/1989 |
| WO | WO/89 08433 | 9/1989 |

OTHER PUBLICATIONS

C.R. Bard: PE Plus Peripheral Balloon Dilatation Catheter, Aug. 1985, *CR Bard, Inc.*

Duprat, et al., *Flexible Balloon–Expanded Stent for Small Vessels, Radiology Journal*, pp. 276–278, 1987.

Maass, et al., *Radiological Follow–Up of Transluminally Inserted Vascular Endoprostheses: an Experimental Study Using Expanding Spirals, Radiology Journal*, pp. 659–663, 1984.

(List continued on next page.)

*Primary Examiner*—Corrine McDermott
*Assistant Examiner*—William H. Matthews
(74) *Attorney, Agent, or Firm*—Fulwider Patton Lee & Utecht, LLP

(57) ABSTRACT

The invention is directed to an expandable stent for implantation in a body lumen, such as a coronary artery or peripheral vein. The stent consists of a plurality of radially expandable cylindrical elements generally aligned on a common longitudinal stent axis and interconnected by one or more interconnecting members placed so as to limit longitudinal contraction during radial expansion. The individual radially expandable cylindrical elements are formed in a serpentine pattern having bends alternating in peaks and valleys designed to expand evenly under radial stress, and to maximize the overall radial expansion ratio. Each peak and valley includes reinforcing members that extend across and proximate to each bend. Sizing and construction of the struts forming the peaks and valleys can create bimodal deployment wherein the struts bend under increasing stresses to enable the stent to expand to larger diameters.

3 Claims, 7 Drawing Sheets

U.S. PATENT DOCUMENTS

| | | |
|---|---|---|
| 4,130,904 A | 12/1978 | Whalen |
| 4,140,126 A | 2/1979 | Choudhury |
| 4,159,719 A | 7/1979 | Haerr |
| 4,323,071 A | 4/1982 | Simpson et al. |
| 4,332,254 A | 6/1982 | Lundquist |
| 4,439,185 A | 3/1984 | Lundquist |
| 4,468,224 A | 8/1984 | Enzmann et al. |
| 4,503,569 A | 3/1985 | Dotter |
| 4,512,238 A | 4/1985 | Balk et al. |
| 4,516,972 A | 5/1985 | Samson |
| 4,531,933 A | 7/1985 | Norton et al. |
| 4,538,622 A | 9/1985 | Samson et al. |
| 4,553,545 A | 11/1985 | Maass et al. |
| 4,554,929 A | 11/1985 | Samson et al. |
| 4,560,374 A | 12/1985 | Hammerslag |
| 4,569,347 A | 2/1986 | Frisbie |
| 4,571,240 A | 2/1986 | Samson et al. |
| 4,572,186 A | 2/1986 | Gould et al. |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,665,918 A | 5/1987 | Garza et al. |
| 4,681,110 A | 7/1987 | Wiktor |
| 4,706,671 A | 11/1987 | Weinrib |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,748,986 A | 6/1988 | Morrison et al. |
| 4,760,849 A | 8/1988 | Kropf |
| 4,762,128 A | 8/1988 | Rosenbluth |
| 4,768,507 A | 9/1988 | Fischell |
| 4,771,777 A | 9/1988 | Horzewski |
| 4,776,337 A | 10/1988 | Palmaz |
| 4,790,315 A | 12/1988 | Mueller, Jr. et al. |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,922,905 A | 5/1990 | Strecker |
| 4,923,464 A | 5/1990 | DiPisa, Jr. |
| 4,950,227 A | 8/1990 | Savin et al. |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,156,619 A | 10/1992 | Ehrenfeld |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,977 A | 3/1993 | Hoffman, Jr. et al. |
| 5,197,978 A | 3/1993 | Hess |
| 5,234,457 A | 8/1993 | Andersen |
| 5,236,446 A | 8/1993 | Dumon |
| 5,593,442 A * | 1/1997 | Klein .................. 623/23.64 |
| 5,674,241 A * | 10/1997 | Bley et al. .................. 606/198 |
| 5,741,327 A | 4/1998 | Frantzen |
| 5,755,781 A | 5/1998 | Jayaraman |
| 5,836,966 A | 11/1998 | St. Germain |
| 5,868,781 A | 2/1999 | Killion |
| 5,922,020 A | 7/1999 | Klein et al. |
| 6,206,911 B1 * | 3/2001 | Milo .................. 623/1.15 |

OTHER PUBLICATIONS

Palmaz, et al., *Expandable Intraluminal Graft: A Preliminary Study, Radiology Journal*, pp. 73–77, 1985.

Wright, et al., *Percutaneous Endovascular Stents: An Experimental Evaluation, Radiology Journal*, pp. 69–72, 1985.

Dotter, *Transluminal Expandable Nitinol Coil Stent Graftin: Preliminary Report, Radiology Journal*, pp. 259–260, Apr. 1983.

Cragg, et al., *Non–Surgical Placement of Arterial Endoprostheses: A New Technique Using Nitinol Wire, Radiology Journal*, pp. 261–263, Apr. 1983.

* cited by examiner

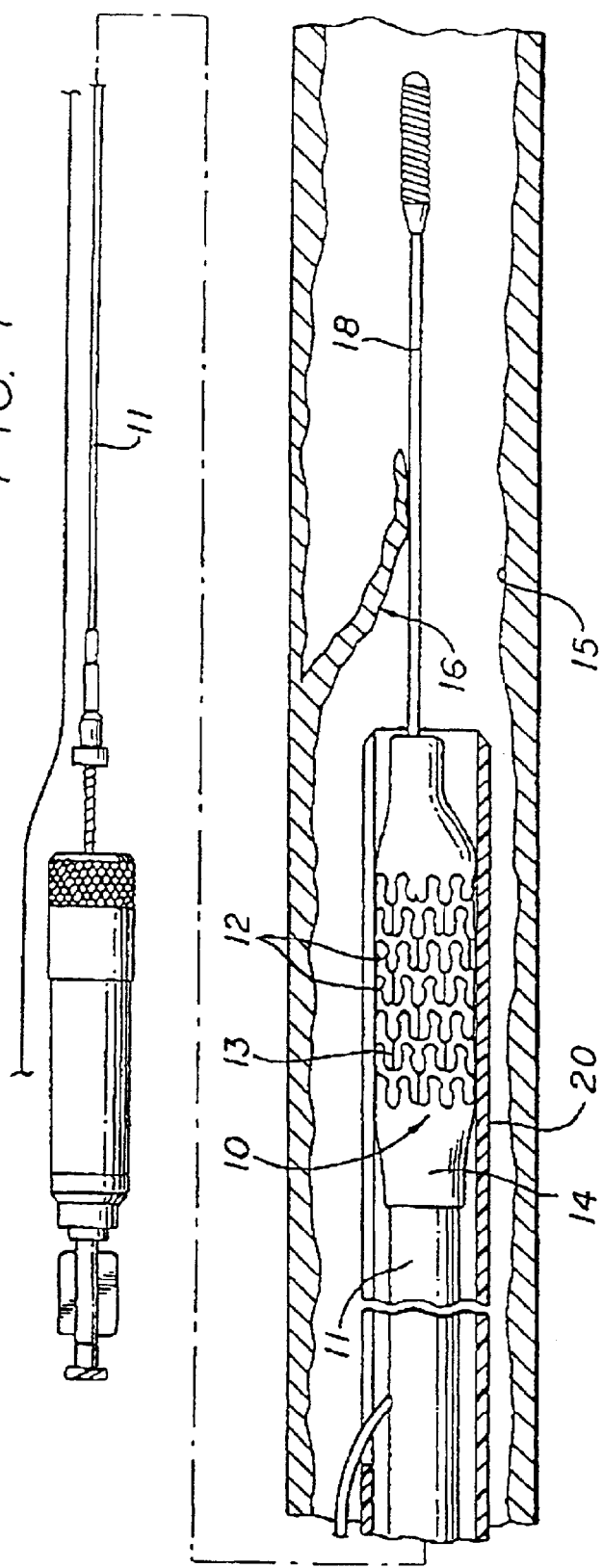
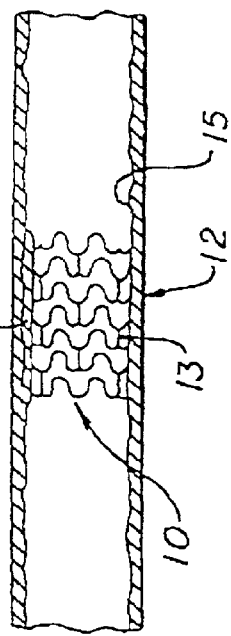
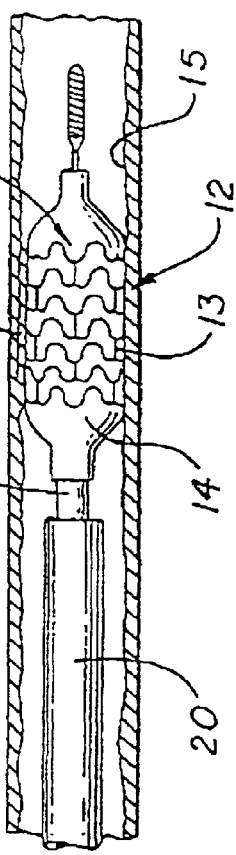

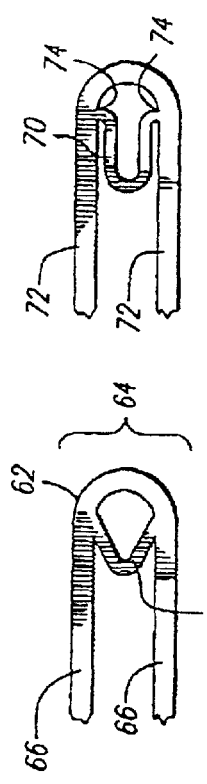
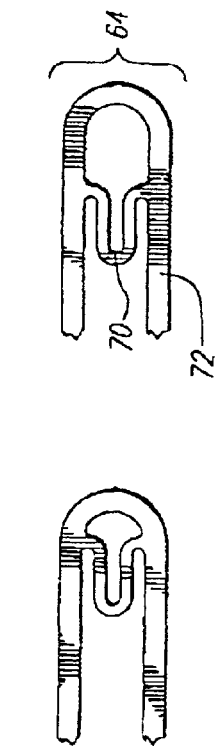
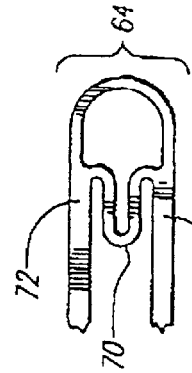
FIG. 7J  FIG. 7K  FIG. 7L
FIG. 7G  FIG. 7H  FIG. 7I
FIG. 7D  FIG. 7E  FIG. 7F
FIG. 7A  FIG. 7B  FIG. 7C

STENT WITH REINFORCED STRUTS AND BIMODAL DEPLOYMENT

This application is a continuation of U.S. Ser. No. 08/881,059 filed Jun. 24, 1997, now abandoned.

BACKGROUND OF THE INVENTION

The present invention relates to expandable endoprosthesis devices, generally called stents, which are adapted to be implanted into a body lumen of a patient, such as a blood vessel, to maintain the patency thereof. These devices are useful in the treatment and repair of atherosclerotic stenoses in blood vessels.

Stents are generally cylindrically-shaped devices which function to hold open and sometimes to expand a segment of a blood vessel or other anatomical lumen. They are particularly suitable for use to support and hold back a dissected arterial lining which, if not so supported and held, can occlude the fluid passageway therethrough.

A variety of devices are known in the art for use as stents and have included: coiled wires in an array of patterns that are expanded after having been placed intraluminally via a balloon catheter; helically-wound coiled springs manufactured from an expandable heat sensitive metal; and self-expanding stents inserted in a compressed state and shaped in a zig-zag pattern. Some more examples are shown in U.S. Pat. No. 4,776,337 to Palmaz; U.S. Pat. No. 4,655,771 to Wallsten; U.S. Pat. No. 4,800,882 to Gianturco; U.S. Pat. No. 4,913,141 to Hillstead; and U.S. Pat. No. 5,292,331 to Boneau.

Such prior art devices include an expandable intraluminal vascular graft that is expanded within a blood vessel by balloon associated with, typically, a dilatation catheter. The graft may be a wire mesh tube, a stainless steel tube with rectangular openings, or a tube with honeycomb style openings. Another prior art device includes a prosthesis for transluminal implantation comprising a flexible tubular body made of flexible thread elements wound together, each thread having a helix configuration.

There are still more conventional endovascular stents. In one design, the wire stent has a generally cylindrical shape, wherein the shape is formed with alternating bent wire loops. Another conventional stent design comprises a series of continuous corrugations compressed together to form a tube-like mesh. Yet another endovascular stent used for the treatment of restenosis is a unitary wire structure, shaped to criss-cross and form a plurality of upper and lower peaks.

One of the difficulties encountered using prior art stents involved maintaining the radial rigidity needed to hold open a body lumen while at the same time maintaining the longitudinal flexibility of the stent to facilitate its delivery. Another problem area was the limiting range of expandability. Certain prior art stents expanded only to a limited degree due to the uneven stresses created upon the stents during radial expansion. This necessitated providing stents having a variety of diameters, thus increasing the cost of manufacture. Additionally, having a stent with a wider range of expandability allowed the physician to re-dilate the stent if the original vessel size was miscalculated.

Another problem with the prior art stents was that the stent contracted along its longitudinal axis upon radial expansion of the stent. This caused placement problems within the artery during expansion.

Various means have been devised to deliver and implant stents. One method frequently described for delivering a stent to a desired intraluminal location involved mounting the expandable stent on an expandable member, such as an inflatable balloon. The balloon was provided on the distal end of an intravascular catheter. The catheter was advanced to the desired location within the patient's body lumen. Inflating the balloon on the catheter deformed the stent to a permanently expanded condition. The balloon was then deflated and the catheter removed.

What has been needed and heretofore unavailable is a stent which has a high degree of flexibility so that it can be advanced through tortuous passageways and can be radially expanded over a wide range of diameters with minimal longitudinal contraction, and yet have the mechanical strength to hold open the body lumen into which it is expanded. There is further a need for a stent-that has high circumferential or hoop strength to improve crush resistance. The present invention satisfies these needs.

SUMMARY OF THE INVENTION

The present invention is directed to an expandable stent having a configuration generally of the type disclosed in U.S. Pat. Nos. 5,569,295 to S. Lam and 5,514,154 to Lau et al., the entire contents of which are incorporated herein by reference. In a preferred embodiment, the present invention stent includes a plurality of adjacent cylindrical elements which are expandable in the radial direction and which are arranged in alignment along a longitudinal stent axis. The cylindrical elements are formed in a serpentine wave pattern transverse to the longitudinal axis and contain a plurality of alternating peaks and valleys.

The present invention also comprises at least one interconnecting member that extends between adjacent cylindrical elements and connects adjacent cylindrical elements to each other. The interconnecting members insure minimal longitudinal contraction of the stent during radial expansion of the cylindrical elements.

The present invention further comprises, in each cylindrical element, a reinforcing member that extends across each peak and valley. More precisely, each peak and each valley of a single cylindrical element is formed by the confluence of two straight struts joining at a bend. The reinforcing member thus spans across the peak or valley, bridging the struts.

The reinforcing member lends strength to the alternating peaks and valleys, wherein the area of maximum stress is at or near the bend. To be sure, the reinforcing member prevents the straight section of the strut from buckling or distorting during expansion of the stent by adding material to a potentially weak area. Furthermore, the size and geometry of the reinforcing member along with the bend may be adjusted so that stress is evenly distributed between the two instead of just being carried by the bend.

Certainly the geometry of the reinforcing member in the present invention can assume many configurations. For example, the reinforcing member could include a loop that curves toward or away from the bend. The reinforcing member could join the struts at a point farther away from or closer to the bend. The reinforcing member can be formed into the bend.

The resulting stent structure is preferably a series of radially-expandable cylindrical elements that are spaced longitudinally close enough to each other so that small dissections in the wall of a body lumen may be pressed back into position by the elements against the lumenal wall, but not so close as to compromise the longitudinal flexibility of the stent. The individual cylindrical elements may rotate slightly relative to adjacent cylindrical elements without significant deformation, cumulatively providing a stent which is flexible along its length and about its longitudinal axis, but which is still very stable in the radial direction in order to resist collapse.

The stent embodying features of the present invention can be readily delivered to the desired lumenal location by mounting it on an expandable member of a delivery catheter, for example a balloon, and by then passing the catheter-stent assembly through the body lumen to the implantation site. A variety of means for securing the stent to the expandable member on the catheter for delivery to the desired location are available. It is presently preferred to compress the stent onto the balloon. Other means to secure the stent to the balloon include providing ridges or collars on the inflatable member to restrain lateral movement, or using temporary, bioabsorbable adhesives.

The present invention by use of the reinforcing members features bimodal deployment. That is, when the stent is expanded radially as described above, it does so in two stages. The first stage is the type of expansion of the stent radially wherein the struts bend slightly outward to accommodate the increasing circumference of each cylindrical element and the loop portion of the reinforcing member is stretched out. The second stage continues from the first stage with the struts continuing to bend outward and with the most severe bending occurring at the reinforcing member until the struts are pulled wide apart to their limits to accommodate the largest diameter that the stent can assume. Further spreading apart of the struts is prevented by the presence of the reinforcing member, which limits the maximum circumferential size attainable by each cylindrical element. By choosing the size and geometry of the reinforcing member and the struts, the amount of force needed to expand the stent to a particular diameter can be altered.

The cylindrical elements of the stent are preferably plastically deformed when expanded (except when nickel-titanium (NiTi) alloys are used as the elements) so that the stent remains in the expanded condition. Therefore, when non-NiTi elements are used, the elements must be sufficiently rigid when expanded to prevent the collapse thereof in use. With super-elastic NiTi alloys, the expansion occurs when the stress of compression is removed which relief causes the phase transformation of the material from the martensite phase back to the expanded austenite phase.

After the stent is expanded, some of the peaks and/or valleys may tip outwardly and become embedded in the vessel wall. Thus, after expansion, the stent does not have a smooth outer wall surface, but rather is characterized by projections which embed in the vessel wall and aid in retaining the stent in place in the vessel.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, depicting a stent embodying features of the invention which is mounted on a delivery catheter and disposed within a body lumen such as a coronary artery.

FIG. 2 is an elevational view, partially in section, similar to that shown in FIG. 1, wherein the stent is expanded within the artery, pressing the dissected lining against the arterial wall.

FIG. 3 is an elevational view, partially in section, showing the expanded stent within the vessel after withdrawal of the delivery catheter.

FIGS. 7(A)–(L) are top plan views of alternative embodiments of a single reinforced peak or valley.

DETAILED DESCRIPTION OF THE PREFERRED EMBODIMENTS

Figure 4:
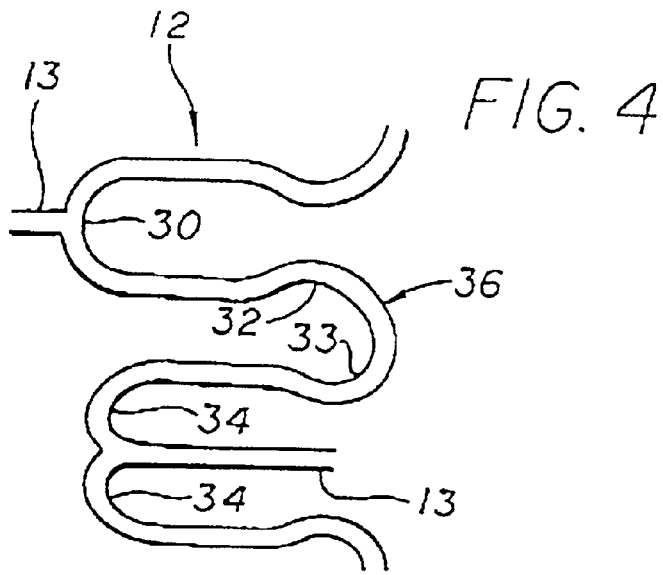
FIG. 4 is an enlarged partial view of the stent of FIG. 5 depicting a serpentine pattern having peaks and valleys that form the cylindrical elements of the stent.

FIG. 1 illustrates stent 10, incorporating features of the invention, which is mounted onto delivery catheter 11. The stent 10 generally comprises a plurality of radially expandable cylindrical elements 12 disposed coaxially and interconnected by members 13 disposed between adjacent cylindrical elements. The delivery catheter 11 has an expandable portion or balloon 14 for expanding stent 10 within an artery 15 or other vessel. The artery 15, as shown in FIG. 1, has a dissected lining 16 which has occluded a portion of the arterial passageway.

The delivery catheter 11 onto which stent 10 is mounted is essentially the same as a conventional balloon dilatation catheter for angioplasty procedures such as percutaneous transluminal angioplasty (PTA) or percutaneous transluminal coronary angioplasty (PTCA). The balloon 14 may be formed of suitable materials such as polyethylene, polyethylene terephthalate, polyvinyl chloride, nylon and ionomers such as those manufactured under the trademark SURLYN by the Polymer Products Division of the Du Pont Company. Other polymers also may be used. In order for stent 10 to remain in place on balloon 14 during delivery to the site of the damage within artery 15, stent 10 is compressed onto the balloon. An elastic protective sheath is sometimes attached around balloon 14 so that stent 10 is crimped onto the sheath, which protects the balloon from the metal stent 10 and insures uniform expansion of the stent when the balloon and elastic sheath are expanded. A retractable protective delivery sleeve 20 also may be provided to further ensure that the stent stays in place on the expandable portion of delivery catheter 11 and to prevent abrasion of the body lumen by the open surface of stent 10 during delivery to the desired arterial location. Other means for securing stent 10 onto balloon 14 also may be used, such as providing collars or ridges on the ends of the working portion, i.e., the cylindrical portion, of the balloon.

Each radially expandable cylindrical element 12 of stent 10 may be independently expanded. Therefore, balloon 14 may be provided with an inflated shape other than cylindrical, e.g., tapered, to facilitate implantation of the stent 10 in a variety of body lumen shapes.

In a preferred embodiment, the delivery of the stent 10 is accomplished in the following manner. The stent 10 is first mounted onto inflatable balloon 14 on the distal extremity of delivery catheter 11. The stent may be "crimped" down onto the balloon to ensure a low profile. The catheter-stent assembly can be introduced within the patient's vasculature in a conventional Seldinger technique through a guiding catheter (not shown). A guidewire 18 is disposed across the arterial section with the detached or dissected lining 16 and then the catheter-stent assembly is advanced over guidewire 18 within artery 15 until stent 10 is positioned within the artery at detached lining 16. The balloon 14 of the catheter is expanded, expanding stent 10 against artery 15, which is illustrated in FIG. 2. While not shown in the drawing, artery 15 preferably can be expanded slightly by the expansion of stent 10 to seat or otherwise fix stent 10 to prevent movement within the artery. In some circumstances during the treatment of stenotic portions of an artery, the artery may have to be expanded considerably in order to facilitate passage of blood or other fluid therethrough.

Stent 10 serves to hold open artery 15 after catheter 11 is withdrawn, as illustrated by FIG. 3. Due to the formation of stent 10 from an elongated tubular member, the undulating component of the cylindrical elements of stent 10 is relatively flat in transverse cross-section, so that when the stent is expanded, the cylindrical elements are pressed into the wall of artery 15 and as a result minimize the development of thrombosis in artery 15. The cylindrical elements 12 of stent 10 which are pressed into the wall of artery 15 eventually will be covered with endothelial cell growth which further minimizes thrombosis. The serpentine pattern of cylindrical sections 12 provide good tacking characteristics to prevent stent movement within the artery. Furthermore, the closely spaced cylindrical elements 12 at regular intervals provide uniform support for the wall of artery 15, and consequently are well adapted to tack up and hold in place small flaps or dissections in the wall of artery 15 as illustrated in FIGS. 2 and 3.

Figure 5:
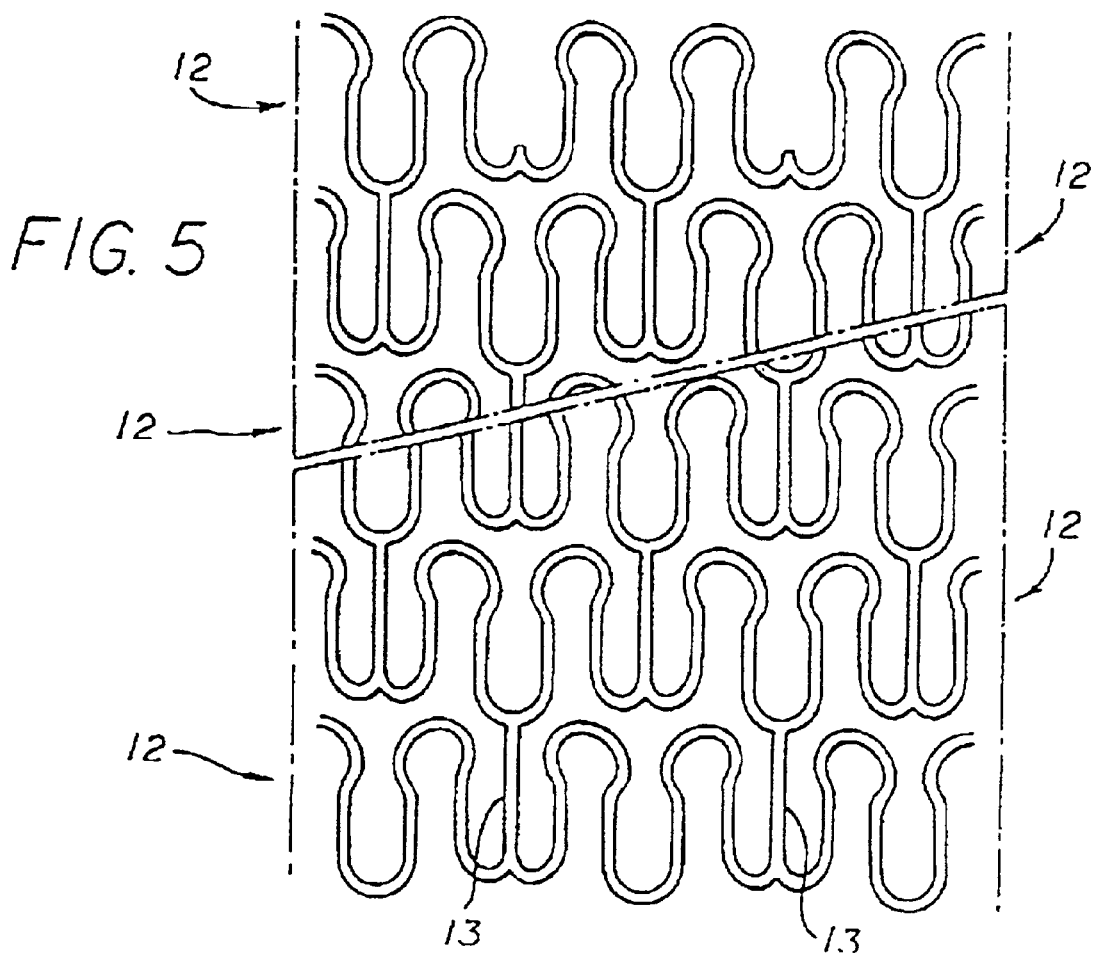
FIG. 5 is a plan view of a flattened section of a stent of the present invention which illustrates the serpentine pattern of the stent.
Figure 6:
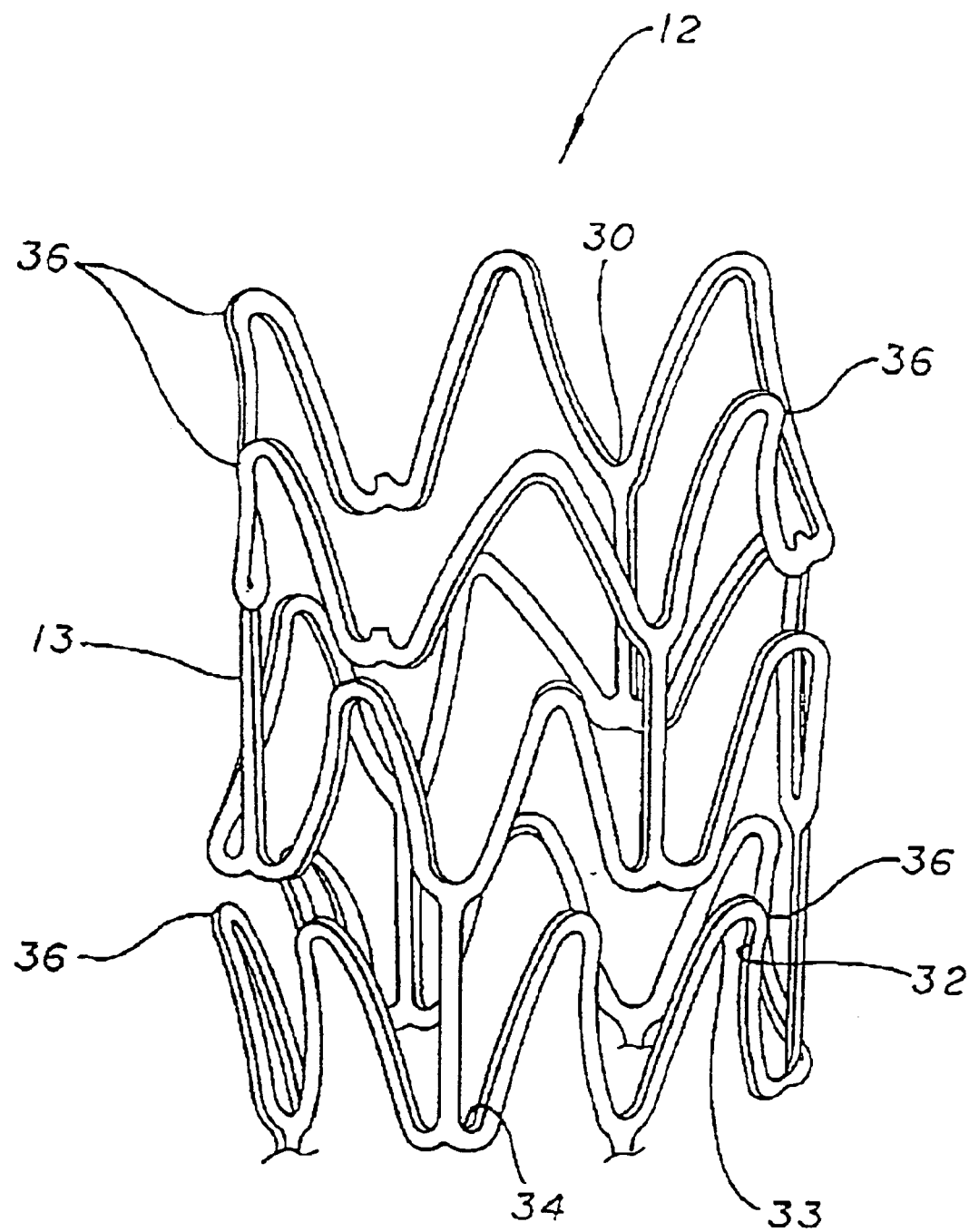
FIG. 6 is a side elevational view of the stent in the expanded condition.

In the preferred embodiment, as depicted in FIGS. 4, 5 and 6, the stresses involved during expansion from a low profile to an expanded profile are much more evenly distributed among the various peaks 36 and valleys 34. As seen in FIG. 4, a portion of cylindrical element 12 of stent 10 illustrates the serpentine pattern having a plurality of peaks and valleys, each having varying radii of curvature, which aids in the even distribution of expansion forces. Interconnecting members 13 serve to connect adjacent valleys of cylindrical element 12 as described above.

After expansion, portions of the various elements will turn outwardly, forming small projections which will embed in the vessel wall. For example, the tip of peak portion 36 tips outwardly upon expansion a sufficient amount to embed into the vessel wall and help secure the implanted stent. Upon expansion, projecting peak 36 provides an outer wall surface on the stent that is not smooth, but instead has a plurality of projecting peaks 36 all along the outer wall surface. While the projections assist in securing the stent in the vessel wall, they are not sharp and thus do not cause trauma or damage to the vessel wall.

One important feature of the present invention is the capability of the stent to expand from a low-profile diameter to a diameter much greater than heretofore was available, while still maintaining structural integrity of the stent in the expanded state. Due to its novel structure, the stent of the present invention has an overall expansion ratio of 1 up to about 4 using certain compositions of stainless steel. For example, a 316L stainless steel stent of the present invention can be radially expanded from a diameter of 1 unit up to a diameter of about 4 units, which deforms the structural members beyond their elastic limits. The stent still retains its structural integrity in the expanded state and it serves to hold open the vessel in which it is implanted. Materials other than 316L stainless steel may give higher or lower expansion ratios without sacrificing structural integrity.

Figure 8:
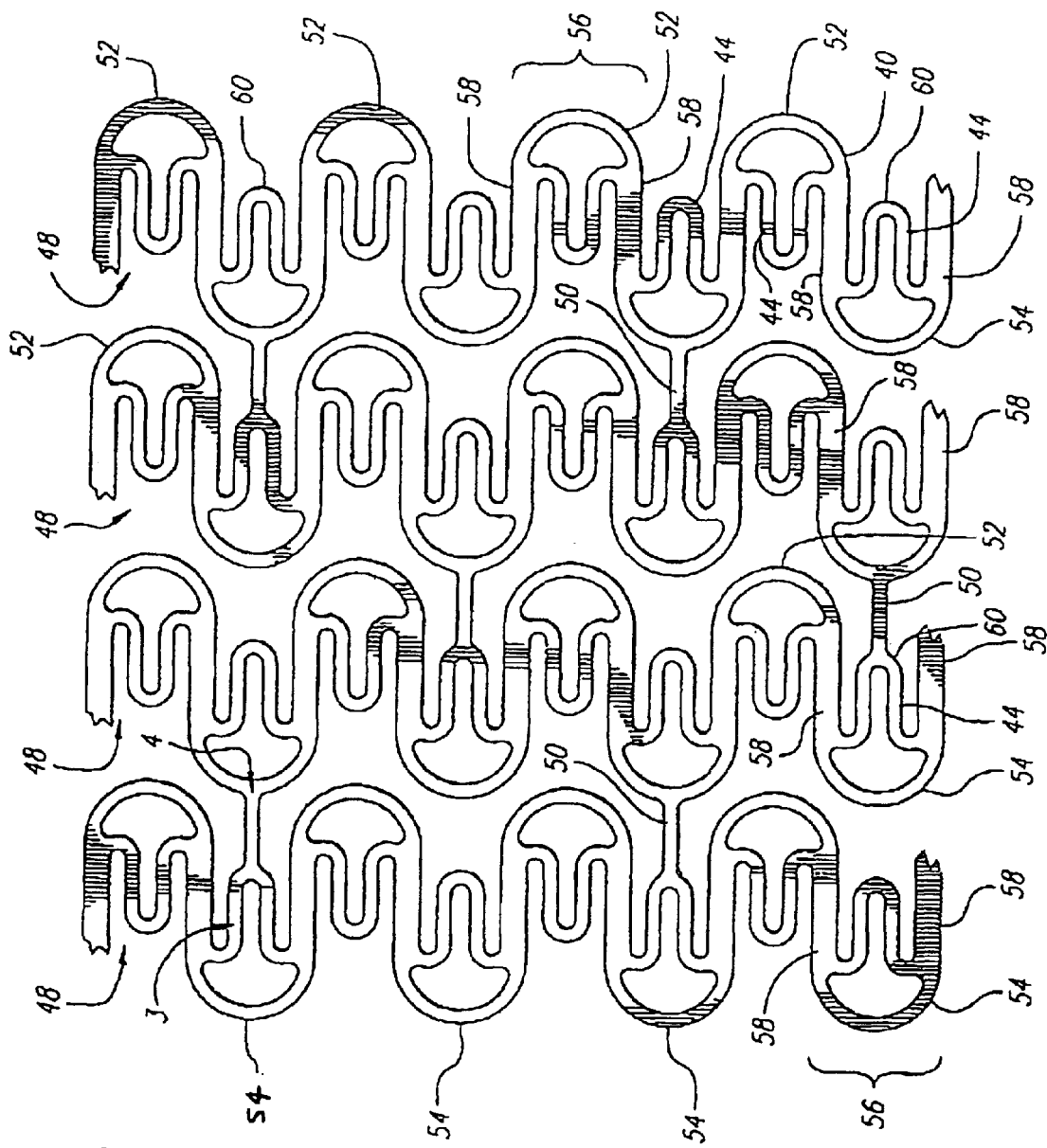
FIG. 8 is a plan view of an alternative embodiment of the present invention reinforced stent.
Figure 9:
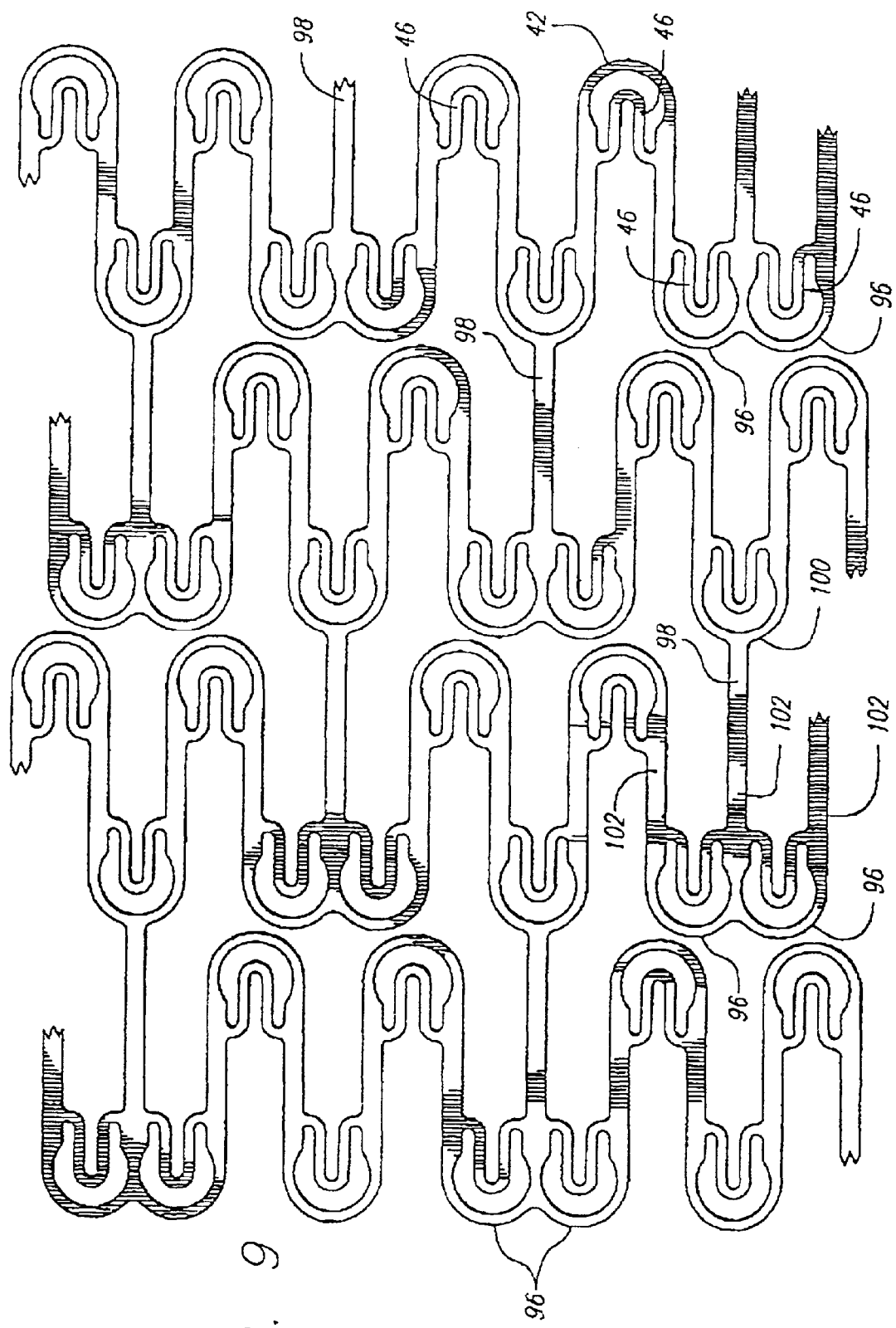
FIG. 9 is another alternative embodiment of the present invention reinforced stent.

FIGS. 8 and 9 are plan views of a flattened section of stents 40, 42 of the present invention, which illustrate the serpentine patterns of the stents as well as varying configurations of reinforcing embers 44, 46. In the preferred embodiment illustrated in FIG. 8, stent 40 is comprised of a plurality of radially expandable cylindrical elements 48 disposed generally coaxially and interconnected by interconnection members 50 which are essentially parallel to the longitudinal stent axis when the stent 40 is in the unexpanded low profile.

As in the earlier described embodiments, the present preferred embodiment shown in FIG. 8 includes alternating peak portions 52 and valley portions 54. Each peak portion 52 or valley portion 54 is essentially a bend 56 interconnecting straight struts 58. In this embodiment, each peak portion 52 or valley portion 54 each cylindrical element is reinforced by reinforcing member 44 extending across bend 56 to interconnect struts 58. In the preferred embodiment depicted in FIG. 8, reinforcing member 44 has an inverted loop 60 that extends in a direction opposite to bend 56. Optionally, interconnecting members 50 may be integrated into loop 60 of reinforcing member 44 as seen in FIG. 9.

The area of peak stress is at or near the apex of bend 56. The present invention provides apparatus for reinforcing this area with reinforcing member 44, which is attached to each side of the bend (i.e., strut 58) away from the apex of bend 56. The width of strut 58 along with the width and geometry of reinforcing member 44 as well as the geometry and dimensions of bend 56 forming peak portion 52 or valley portion 54 can be adjusted to distribute the stress between bend 56 and reinforcing member 44. Furthermore, varying the base material of the stent would affect the design of bend 56 and reinforcing member 44.

In FIG. 7, a variety of alternative embodiments of a peak portion or valley portion of a stent are shown. Specifically, reinforcing members of different constructions are shown in plan views. As seen in FIG. 7(A), peak portion or valley portion 62 is formed by a bend 64 supported by struts 66. Reinforcing member 68 has a V shape and is integrated into bend 64. FIGS. 7(B) and (C) show varying bend thicknesses. FIG. 7(D) illustrates a reinforcing member 70 that intersects struts 72 wherein the point of intersection creates sharpened corners 74 that are rounded in FIGS. 7(B), (C), (E), and (F). In FIGS. 7(E) and (F), reinforcing member 70 has been moved farther down struts 72 away from bend 64. FIG. 7(G) depicts an alternative embodiment wherein reinforcing member 76 has been integrated into bend 78. In FIG. 7(H), reinforcing member 80 includes loop 82 that has been pinched together. FIG. 7(I) is a plan view of an alternative embodiment reinforcing member 84 that has been integrated into bend 86 although slits 88 have been formed in the base material. In FIGS. 7(J), (K) and (L), the shape of open areas 90, 92 have been adjusted to vary the strength at different parts of the stent. Moreover, in FIGS. 7(J), (K) and (L), reinforcing member 94 has its orientation reversed as compared to the reinforcing members in the previous embodiments.

FIG. 9 is a plan view of an alternative embodiment stent 42 wherein the pattern of peaks and valleys have been modified to provide multiple side-by-side valley portions 96. Furthermore, interconnecting member 98 is attached to bend 100 and transitions into a strut 102 at an opposite end.

Figure 10A:
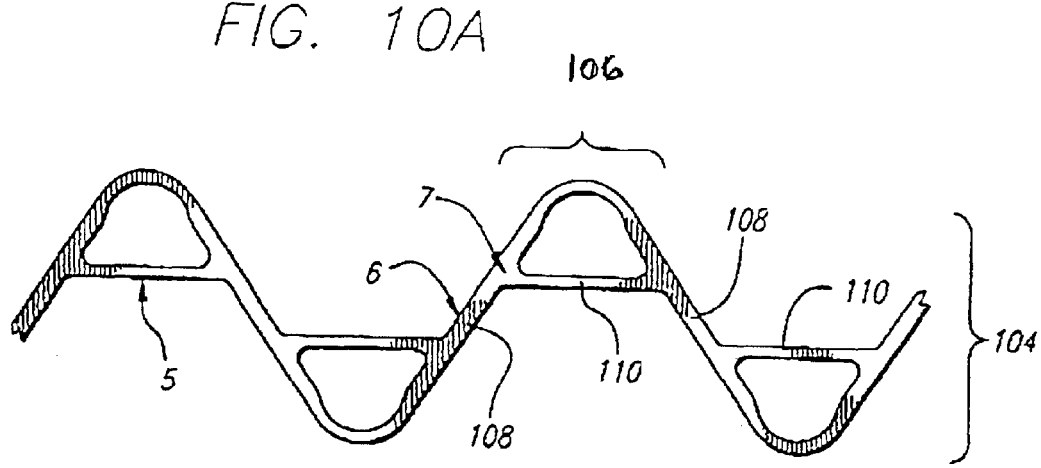
FIGS. 10(A) and (B) show the bimodal deployment of a preferred embodiment stent.

The present invention further includes a bimodal feature as illustrated in FIGS. 10(A) and (B). FIG. 10(A) shows a single cylindrical element 104 having alternating peaks and valleys, wherein each peak and valley is formed by bend 106 joining two struts 108. In the conditions shown in FIG. 10(A), struts 108 have been slightly bent, which is the result of a first stage expansion of the stent thereby increasing the circumference of the stent. Thus, struts 108 are no longer parallel and have spread outwards. Reinforcing member 110 helps maintain the angle formed by struts 108.

Also, FIG. 10(A) shows the first mode in which reinforcing member 110 straightens and locks into position; the loop or kink previously formed in reinforcing member 110 is straightened. Reinforcing member 110 in this configuration provides substantial strength and stiffness to the stent.

Figure 10B:
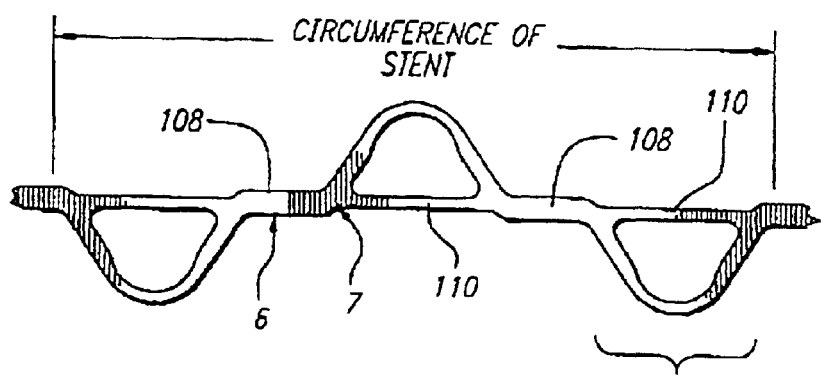

In FIG. 10(B), the stent has been expanded to a second stage thereby increasing the circumference of the stent to a greater degree than that shown in FIG. 10(A). As the stent is expanded further, struts 108 bend at the intersections with reinforcing members 110 until they are aligned with the circumference of the stent as shown in FIG. 10(B). At this point, the stent is fully deployed to its maximum diameter. Accordingly, struts 108 have been pulled straight and are nearly paralleled with reinforcing member 110. In this mode, the stent has reached its maximum circumference; further increases in the stent can conceivably be achieved by deformation in struts 108 and reinforcing member 110. Essentially, the circumference of the stent can be increased by stretching struts 108 and reinforcing members 110 further.

It is possible to deploy the stent and reinforcing member with or without two distinct modes. This behavior is controlled by the force required to bend struts 108 at their intersection with reinforcing member 110 as compared to the force required to bend and open the loop in the reinforcing member 110. The behavior can be controlled by the relative widths and lengths of the various structures.

The tubing may be made of suitable biocompatible material such as stainless steel, titanium, tantalum, super-elastic nickel-titanium (NiTi) alloys and even high strength thermoplastic polymers. The stent diameter is very small, so the tubing from which it is made must necessarily also have a small diameter. For PCTA applications, and as an example only, typically the stent has an outer diameter on the order of about 0.065 inches (0.165 cm) in the unexpanded condition, the same outer diameter of the tubing from which it is made, and can be expanded to an outer diameter of about 0.200 inches (0.508 cm) or more. The wall thickness of the tubing is about 0.003 inches (0.008 cm). For stents implanted in other body lumens, such as in non-coronary PTA applications, the dimensions of the tubing forming the stent are correspondingly larger. The dimensions of the stent will vary depending upon the application and body lumen diameter in which the stent will be implanted.

In the instance when the stent is made from plastic, it may have to be heated within the arterial site where the stent is expanded to facilitate the expansion of the stent. Once expanded, it would then be cooled to retain its expanded state. The stent may be conveniently heated by heating the fluid within the balloon or the balloon directly by a known method. The stent may also be made of materials such as super-elastic NiTi alloys. In this case the stent would be formed full size but deformed (e.g. compressed) into a smaller diameter onto the balloon of the delivery catheter to facilitate transfer to a desired intraluminal site. The stress induced by the deformation transforms the stent from a austenite phase to martensite phase and upon release of the force, when the stent reaches the desired intraluminal location, the stent expands due to the transformation back to the austenite phase.

While the invention has been illustrated and described herein in terms of its use as an intravascular stent, it will be apparent to those skilled in the art that the stent can be used in other instances in all vessels in the body. Since the stent of the present invention has the novel feature of expanding to very large diameters while retaining its structural integrity, it is particularly well suited for implantation in almost any vessel where such devices are used. This feature, coupled with limited longitudinal contraction of the stent when it is radially expanded, provides a highly desirable support member for all vessels in the body. Other modifications and improvements may be made without departing from the scope of the invention.

What is claimed is:

1. A flexible stent for implantation in a body lumen and expandable from a contracted condition to an expanded condition, comprising:

a plurality of adjacent cylindrical elements which are expandable in the radial direction and arranged in alignment along a longitudinal stent axis;

the cylindrical elements formed in a serpentine wave pattern transverse to the longimdinal axis and containing a plurality of alternating peaks and valleys;

at least one interconnecting member extending between adjacent cylindrical elements and connecting them to one another;

at least one reinforcing member extending across a width of the alternating peaks and valleys such that the reinforcing member is curved and has a circumferential width when the stent is in the contracted condition;

each reinforcing member lying in the same circumferential plane as the cylindrical elements and having a configuration essentially parallel to the longitudinal stent axis when the stent is in the contracted condition; and the serpentine pattern having varying degrees of curvature in regions of the peaks and valleys adapted so that radial expansion of the adjacent cylindrical elements is substantially uniform around a circumference of the cylindrical elements during expansion of the stent from the contracted condition to the expanded condition;

wherein the circumferential width of each reinforcing member is smaller than the width of the peak or valley it extends across;

wherein each of the alternating peaks and valleys has one of said reinforcing members extending across its width.

2. A flexible stent for implantation in a body lumen and expandable from a contracted condition to an expanded condition, comprising:

a plurality of adjacent cylindrical elements which are expandable in the radial direction and arranged in alignment along a longitudinal stent axis;

the cylindrical elements formed in a serpentine wave pattern transverse to the longitudinal axis and containing a plurality of alternating peaks and valleys;

at least one interconnecting member extending between adjacent cylindrical elements and connecting them to one another;

at least one reinforcing member extending across a width of the alternating peaks and valleys such that the reinforcing member is curved and has circumferential width when the stent is in the contracted condition;

each reinforcing member lying in the same circumferential plane as the cylindrical elements and having a configuration essentially parrallel to the longitudinal stent axis when the stent is in the contracted condition; and the serpentine patter having varying degrees of curvature in regions of the peaks and valleys adapted so that radial expansion of the adjacent cylindrical elements is substantially uniform around a circumference of the cylindrical elements during expansion of the stent from the contracted condition to the expanded condition;

wherein the circumferential width of each reinforcing member is smaller than the width of the peak or valley it extends across;

wherein the interconnecting member connects a reinforcing member of a valley of one cylindrical element with a valley of an adjacent cylindrical element.

3. A flexible stent for implantation in a body lumen and expandable from a contracted condition to an expanded condition, comprising:

a plurality of adjacent cylindrical elements which are expandable in the radial direction and arranged in alignment along a longitudinal stent axis;

the cylindrical elements formed in a serpentine wave pattern transverse to the longitudinal axis and containing a plurality of alternating peaks and valleys;

at least one interconnecting member extending between adjacent cylindrical elements and connecting them to one another;

at least one reinforcing member extending across a width of the alternating peaks and valleys such that the reinforcing member is curved and has a circumferential width when the stent is in the contracted condition;

each reinforcing in member lying in the same circumferential plane as the cylindrical elements and having a configuration essentially parallel to the longitudinal stent axis when the stent is in the contracted condition; and the serpentine pattern having varying degrees of curvature in regions of the peaks and valleys adapted so that radial expansion of the adjacent cylindrical elements is substantially uniform around a circumference of the cylindrical elements during expansion of the stent from the contracted condition to the expanded condition;

wherein the circumferential width of each reinforcing member is smaller than the width of the peak or valley it extend across;

wherein the reinforcing member is comprised of a first quarter turn that transitions into a half turn, which transitions into a second quarter turn.

* * * * *

UNITED STATES PATENT AND TRADEMARK OFFICE
CERTIFICATE OF CORRECTION

PATENT NO. : 6,773,455 B2
DATED : August 10, 2004
INVENTOR(S) : Richard T. Allen and Daniel L. Cox It is certified that error appears in the above-identified patent and that said Letters Patent is hereby corrected as shown below:

Column 6,
Line 4, delete "embers" and insert -- members --.
Line 16, delete "each cylindrical" and insert -- in each cylindrical --.

Column 8,
Line 22, delete "longimdinal" and insert -- longitudinal --.

Column 10,
Line 5, delete "reinforcing in" and insert -- reinforcing --.

Signed and Sealed this

Eighth Day of February, 2005

JON W. DUDAS
*Director of the United States Patent and Trademark Office*